United States Patent

Nakano et al.

[11] Patent Number: 5,001,245
[45] Date of Patent: Mar. 19, 1991

[54] PROCESS FOR PRODUCING METALLIC SALT OF ETHERCARBOXYLIC ACID

[75] Inventors: Masao Nakano, Hyogo; Miaki Asakawa; Yusei Nagamura, both of Himeji; Akio Fukui, Fujisawa; Yoichi Nakagawa, Takarazuka, all of Japan

[73] Assignee: Nippon Shokubai Kagaku Kogyo Company, Ltd., Osaka, Japan

[21] Appl. No.: 309,164

[22] Filed: Feb. 13, 1989

[30] Foreign Application Priority Data

Feb. 12, 1988 [JP] Japan .................. 63-28660
Jan. 10, 1989 [JP] Japan .................. 1-1930

[51] Int. Cl.$^5$ .......... C07F 3/04; C07F 3/06; C07C 59/305; C07C 51/347
[52] U.S. Cl. .................. 556/131; 562/579; 562/582.583; 562/585; 562/587; 562/589; 252/89.1
[58] Field of Search ............ 562/583, 579, 582, 585, 562/587, 589; 556/131, 133

[56] References Cited

U.S. PATENT DOCUMENTS

| | | | |
|---|---|---|---|
| 3,692,685 | 4/1972 | Lamberti et al. | 252/89 |
| 3,862,219 | 1/1975 | Lindsay et al. | 562/583 |
| 3,954,858 | 5/1976 | Lamberti et al. | 562/583 |
| 4,058,560 | 11/1977 | Walter | 562/583 |
| 4,223,162 | 9/1980 | Crutchfield et al. | 562/583 |
| 4,639,325 | 1/1987 | Valenty et al. | 252/89.1 |
| 4,827,028 | 5/1989 | Scardera et al. | 562/583 |

FOREIGN PATENT DOCUMENTS

| | | |
|---|---|---|
| 0236007 | 9/1987 | European Pat. Off. |
| 266723 | 5/1988 | European Pat. Off. |
| 2738825 | 3/1978 | Fed. Rep. of Germany |
| 1389732 | 4/1975 | United Kingdom |

*Primary Examiner*—Werren B. Lone
*Assistant Examiner*—Vera C. Clarke
*Attorney, Agent, or Firm*—Oblon, Spivak, McClelland, Maier & Neustadt

[57] ABSTRACT

A preparation of metallic salt of ethercarboxylic acid in a pure form by restraining the formation of fumaric acid likely to occur when maleic acid and/or maleic anhydride react with oxycarboxylic acid. The ethercarboxylic product is a useful chelating agent.

14 Claims, No Drawings

PROCESS FOR PRODUCING METALLIC SALT OF ETHERCARBOXYLIC ACID

BACKGROUND OF THE INVENTION

The present invention relates to a process for producing metallic salt of ethercarboxylic acid (hereinafter referred to as "ethercarboxylic product") useful as an organic chelating agent. More particularly, the present invention relates to the preparation of ethercarboxylic product in a highly pure form by restraining the formation of fumaric acid likely to occur in the manufacture of the product when maleic acid reacts with oxycarboxylic acid.

Ethercarboxylic products are known for their strong chelating ability by which metallic ions are confined in rings; particularly tetrasodium tartrate monosuccinate (I) and hexasodium tartrate disuccinate (II) are known as useful detergent builders, the formulas of these two salts are respectively as follows:

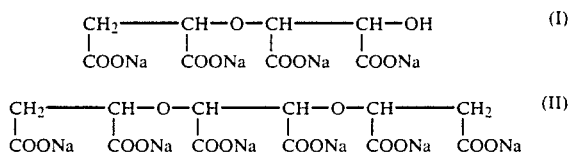

The production of metallic salt of ethercarboxylic acid is suggested in many literatures. U.S. Pat. Nos. 4,058,560, 4,188,493 and British Patent No. 1,389,732 disclose processes for manufacturing salts of carboxymethyloxy succinic acids. EP No. 236,007 discloses the preparation of salts of oxydisuccinic acid, and U.S. Pat. No. 4,663,071 and EP No. 266,723 disclose the preparation of salts of tartaric monosuccinic acids and tartaric disuccinic acids with the use of maleic acid and tartaric acid, and the adaptation of them for detergent builders. In common with these known processes, oxycarboxylic acids such as glycolic acid, malic acid, tartaric acid or tartronic acid, and maleic acid are reacted in the presence of zinc and/or alkaline earth metal, to which alkali metal hydroxide is added until the pH value is raised to 10 to 13. The reaction takes place at a concentration of 20 to 60 wt % organic acid salt, at a temperature of 50° to 120° C. over a period of 0.5 to 10 hours. In this way metallic salt of ethercarboxylic acid is obtained. Then alkali metal carbonate is added to remove the zinc and/or alkaline earth metal as zinc carbonate and/or alkaline earth metallic carbonate. Being free from the zinc and/or alkaline earth metal, the alkali metal salt of ethercarboxylic acid becomes useful as a detergent builder.

Under the known processes mentioned above, insoluble organic acid salts are produced in the reaction between the carboxylic acids and the metals. On the other hand, as the concentration of these organic acid salts becomes high, the ethercarboxylic product reaches a state of equilibrium for a shorter period of time, thereby securing a high yield of the product. However, if the industrial-scale process is carried out at such a high concentration from the start to the end, the viscosity becomes high because of a large amount of insoluble substances, thereby making it difficult to stir the mixture. In addition, heat is generated by neutralization between the acid and the base. There arises a need for dissipating the heat. In this way the process encounters with the difficulty in stirring and the necessity of dissipating the heat, which obstructs the smooth prosecution of the process. The known process is carried out at a reduced concentration so as to secure the smooth stirring and quick heat dissipation even though the yield is sacrificed.

Commercial oxycarboxylic acids such as malic acid, glycolic acid and tartaric acid are generally on sale in solid. To put them in industrial use, they are diluted with water before starting an addition reaction. However oxycarboxylic acids are generally manufactured in aqueous solution. If they are used in aqueous solution, it will be unnecessary to concentrate the aqueous solution and then dry into solids.

One proposal is to supply the material in the form of a slurry, and to concentrate it to the extent that the stirring and heat dissipation are not prevented. Then the addition reaction is carried out. However, it has been found that the concentrating of the slurry involves the formation of fumaric acid, which is difficult to react with oxycarboxylic acids. This leads to the low yield of ethercarboxylic products, and also makes it difficult to obtain them in a pure state. There seems to be at least two reasons for the formation of fumaric acid; one is that maleic acid is subjected to cis-trans isomerism and transform into fumaric acid, and the other is that the metallic salts of ethercarboxylic acid is subjected to a reversible reaction, thereby decomposing into the original oxycarboxylic acid and maleic acid. About 50% of unsaturated acids becomes fumaric acid while the decomposition proceeds.

In the addition reaction mentioned above zinc and/or alkaline earth metal are normally added, but these substances produce zinc salt of ethercarboxylic acid and/or alkaline earth metallic salt. However, alkali metal salts of ethercarboxylic acid are known as useful detergent builders, but zinc salt and/or alkaline earth metallic salt of ethercarboxylic acid are not useful as detergent builders. On the other hand, all these metallic salts are useful as chelating agents, which captures heavy metals. As a result, the present invention aims at utilizing the chelating ability of alkali metal salt, zinc salt of ethercarboxylic acid and/or alkaline earth metallic salts.

The ethercarboxylic products find many applications, and as an example the manner of using it as a detergent builder will be described:

As described above, zinc salts and/or alkaline earth metallic salts are not useful as detergent builder. To remove such useless substances a special process is required. However, if zinc and alkaline earth metals are removed in the form of salts, it leads to the low yield of ethercarboxylic product. As a result, it is necessary to substitute zinc salt and/or alkaline earth metal with alkali metal. To substitute these metals, alkali metal carbonate and/or bicarbonate is added to zinc salt and/or alkaline earth metallic salt of ether carboxylic acid. The zinc carbonate and/or alkaline earth metallic carbonates are removed as sediments by decanting or any other similar method. However, the removal of these useless substances unavoidably involves the discharge of ethercarboxylic acid in the form of alkali metal salt. This not only leads to the low yield of ethercarboxylic product but also to pollution problems and waste of resources.

SUMMARY OF THE INVENTION

The present invention aims at solving the problems pointed out above, and is to provide a process for manufacturing ethercarboxylic product at a high yield on a simplified process.

Another object of the present invention is to provide a process for manufacturing ethercarboxylic product useful as a detergent builder, with the effective recovery of zinc and/or alkaline earth metal for recycling.

Other objects and advantages of the present invention will become more apparent from the following detailed description, when taken in conjunction with the examples given below for the purpose of illustrating embodiments in accordance with the present invention.

According to the present invention there is provided a process for producing ethercarboxylic products, the process comprising concentrating an aqueous solution containing (a) maleic acid and/or maleic anhydride, (b) oxycarboxylic acid, alkali metal, and (c) zinc and/or alkaline earth metal, wherein the equivalent of the total base equivalent of (c) alkali metal and (d) zinc and/or alkaline earth metal to the total acid equivalent of (a) maleic acid and/or maleic anhydride, and (b) oxycarboxylic acid falls in the range of 0.93 to 1.04, adding alkali metal to adjust the above-mentioned equivalent ratio to the range of 1.05 to 2.0 so as to effect an addition reaction between the maleic acid and the oxycarboxylic acid.

Maleic acid as the material can be either in the form of free acid or in the form of salt of alkali metal, zinc or alkaline earth metal. Alternatively it can be maleic anhydride. In addition, the maleic acid, its salt or maleic anhydride can be in solid, slurry, or solution. Alternatively, a recovered substance can be reused as described below.

Oxycarboxylic acid can be glycolic acid, tartaric acid, malic acid, tartronic acid, glyceric acid, lactic acid, or oxypropionic acid. Alternatively, alkali metal, zinc salt or alkaline earth metallic salt produced in the manufacture of oxycarboxylic product can be utilized. These materials can be in any form such as solid, slurry or solution. Particularly, tetrasodium tartrate monosuccinate (I) and hexasodium tartrate disuccinate (II) are useful as detergent builder materials, which are obtainable when tartaric acid is used.

Alkali metal such as sodium or potassium is used as hydroxide.

Zinc and alkaline earth metal such as calcium, magnesium, strontium and barium are used singly or in combination. These metals are used as hydroxide, oxide and carbonate. Zinc and/or alkaline earth metal is frequently taken in the metallic salt of ethercarboxylic acid, which is transformed into alkali metal when they are used as detergent builders. However, it is not necessary to remove it if these metals are used to chelate heavy metals.

In the present invention (a) maleic acid and/or maleic anhydride, (b) oxycarboxylic acid, (c) alkali metal and (d) zinc and/or alkaline earth metal are mixed to prepare an aqueous mixture in which the above-mentioned equivalent ratio falls in the range of 0.93 to 1.04, preferably 0.96 to 1.02. One example of the feasible processes is that maleic acid is mixed with an aqueous solution containing an industrial salt of oxycarboxylic acid and alkali metal (e.g. sodium hydroxide), zinc and/or alkaline earth metal (e.g. calcium hydroxide) are added thereto such that the above-mentioned equivalent raio falls in the range mentioned above.

If the above-mentioned equivalent ratio is smaller than 0.93, cis-trans isomerization is likely to occur, thereby producing fumaric acid. If it exceeds 1.04, the addition reaction between maleic acid and oxycarboxylic acid proceeds while the concentrating is in progress. Since the addition reaction proceeds toward equilibrium, the metallic salt of ethercarboxylic acid is reversibly decomposed into oxycarboxylic acid and unsaturated acids (at the ratio of maleic acid to fumaric acid is virtually 1:1). The addition reaction between fumaric acid and oxycarboxlic acid does not proceed at all or proceed only at a negligible speed. If it takes a long period of time to complete the concentration, it results in the undesirable formation of fumaric acid, thereby reducing the yield and purity of the ethercarboxylic products. However, when the concentration takes place with the above-mentioned equivalent ratio falling in the range of 0.93 to 1.04, maleic acid is advantageously slow in transforming into fumaric acid even if it occurs. Another advantage is that the rate of the addition reaction between maleic acid and oxycarboxylic acid is decreased, which means that a decomposition of ethercarboxylic acid is retarded. The period of time and the temperature are adjustable in a pretty wide range for effecting the concentration.

The mole ratio of maleic acid and/or maleic anhydride:oxycarboxylic acid:zinc and/or alkaline earth metal is 0.2–10:1:0.1–5, wherein it is preferred that the molar volume of zinc and/or alkaline earth metal is not greater than the total molar volume of maleic acid and/or maleic anhydride and oxycarboxylic acid.

Then the aqueous mixture is concentrated if desired, under a reduced pressure at a temperature of 20° to 120° C., preferably 40° to 90° C., over a period of 0.5 to 48 hours. The degree of concentration is adjusted to ensure that the stirring and the heat disspating can be smoothly carried out. The aqueous mixture is preferably concentrated until the concentration of alkali metallic salts reaches 20 wt % or more, preferably 45 wt % or more, wherein the concentration is calculated on the presumption that all of carboxylic groups are changed to alkali metal salts.

After the aqueous mixture is appropriately concentrated, alkali metal is added to enable the above-mentioned equivalent ratio to fall in the range of 1.05 to 2.0, preferably 1.10 to 1.50. If it is smaller than 1.05, the addition reaction between maleic acid and oxycarboxylic acid does not proceed. Whereas, if it exceeds 2.0, the ethercarboxylic products are rapidly decomposed into oxycarboxylic acid and unsaturated acid (maleic acid and fumaric acid), thereby increasing the amount of fumaric acid. In this way the purity and the yield of ethercarboxylic products are reduced.

Alkali metal such as sodium or potassium are used as hydroxides such as sodium hydroxide or potassium hydroxie.

As the addition reaction proceeds, the viscosity of the reaction mixture decreases, thereby facilitating the stirring. While the reaction proceeds, the mixture is preferably concentrated so that the ethercarboxylic products reache equilibrium in a relatively short period of time. The reaction temperature is in the range of 20° to 120° C., preferably 40° to 90° C., and the reaction time is 0.5 to 20 hours.

In this way ethercarboxylic products are produced. After the reaction is finished, inorganic acid (e.g. hydrochloric acid, sulfuric acid, carbonic acid, etc.) or organic acid (e.g. oxalic acid, acetic acid, tartaric acid, etc.) is added to the reaction mixture, and/or water is poured to dilute it. If necessary, the mixture is cooled, thereby allowing metallic salts of unreacted oxycarboxylic acid including alkali metal salt and zinc salt and/or alkaline earth metallic salt to precipitate. The purity of the product is enhanced.

The obtained ethercarboxylic product contains salts of alkali metals and zinc and/or alkaline earth metals, and it is required to remove zinc and/or alkaline earth metals if the product is to be used as a detergent builder. The zinc and/or alkaline earth metals are removed by contacting alkali metal carbonates or bicarbonate with the zinc and/or alkaline earth metals so as to form zinc carbonae and/or alkaline earth metallic carbonates. In this way the ethercarboxylic products are obtained in a pure form. Nevertheless, the waste zinc carbonate and/or alkaline earth metallic salt contain some amount of ethercarboxylic products, zinc salt and/or alkaline earth metallic salt. Under the present invention zinc and/or alkaline earth metals are recovered and recycled, thereby reducing the discharge of harmful industrial waste. A high yield of the metallic salts of carboxylic acid is secured.

The process of the present invention will be described in greater detail:

Alkali metal carbonate and/or bicarbonate is added to the ethercarboxylic products so as to cause the zinc carbonate and/or alkaline earth metallic carbonate to precipitate, thereby obtaining the products in a pure form. The zinc carbonate and/or alkaline earth metallic carbonate are recovered, and reacted with maleic acid and/or maleic anhydride to give zinc and/or alkaline earth metallic salt of malec acid in an aqueous medium. The resulting mixture is recycled for starting the addition reaction.

The contact between the formative products and the alkali metal carbonate and/or bicarbonate is effected at a temperature of 60° to 100° C. The precipitated zinc carbonates and/or alkaline earth metallic carbonates are removed, and the desired ethercarboxylic products are obtained. It is preferred to remove an unreacted oxycarboxylic acid beforehand. The alkali metals can be sodium, potassium, etc. as mentioned above. The contact between the formative products and the alkali metal carbonate and/or bicarbonate is effected by stirring the products with the addition of the alkali metal carbonate or hydrogencarbonate, or alternatively, by stirring an aqueous solution containing the alkali metal carbonate and/or bicarbonate with the addition of the product. While the products are in contact with the alkali metal carbonate and/or bicarbonate, the zinc and/or alkaline earth metals contained in the products precipitate in the form of carbonates, and the ethercarboxylic acids remain in the aqueous solution in the form of alkali metal salts. The precipitated zinc and/or alkaline earth metal carbonates are separated by a decanting method, a filtering method or any other suitable method. In this way the ethercarboxylic products are obtained as an aqueous solution.

As described above, the zinc carbonate and/or alkaline earth metal carbonates are recovered, and reacted with maleic acid and/or maleic anhydride in an aqueous medium at a relatively high temperature such as 50° to 90° C., and is preferably allowed to stand at a pH value of 7 or less. It is preferred that the mixture is fully stirred so as to diffuse the carbonate particles as widely as possible. Carbon dioxide is generated when the mixture is in reaction, and it can be recovered by absorption with alkali metal hydroxide aqueous solution in the form of alkali metal carbonates and bicarbonates, which can be recycled. Under the present invention zinc and/or alkaline earth metals are recovered and recycled by the use of maleic acid and/or maleic anhydride, which are used to initiating the addition reaction. As a result, there is no waste of useful materials, which also avoids environmental contamination problems. Some amount of metallic salts of ethercarboxylic acid are discharged together with the slurry of zinc carbonate and/or alkaline earth metal carbonate, but it is also recovered and recycled together with zinc and/or alkaline earth metals. The waste of resources is prevented.

EXAMPLE 1

346 kg (500 moles) of a 28 wt % aqueous solution of disodium DL-tartarate, 46.6 kg (475 moles) of maleic anhydride, 83.4 kg (450 moles) of 40 wt % calcium hydroxide slurry, and 4.2 kg (50 moles) of a 48 wt % aqueous solution of sodium hydroxide were mixed in a reactor (500 l capacity). The equivalent ratio of the base equivalent to the acid equivalent of the mixture was 1.00, and the pH value was 8.7. The high-performance liquid chromatographic analysis showed that the organic acid salt had a concentration of 36.0 wt %.

The mixture was concentrated to 279.0 kg at a reduced pressure at 70° C. over a period of three hours. 22.8 kg (273 moles) of a 48 wt % aqueous solution of sodium hydroxide was added to raise the equivalence ratio acid equivalent to 1.14, and the mixture was reacted while the concentrating is in progress at at 75° C. over a period of eight hours. The concentration was 61.6 wt %.

To remove an unreacted tartaric acid from the product, 103.4 kg of water and 3.8 kg (25 moles) of DL-tartaric acid were added and the mixture was stirred and allowed to stand at 30° C. for a day (24 hours). Then the precipitated calcium tartrate was filtered. The cake (calcium tartrate) was used in the example (2).

99.1 kg of water, 14.1 kg (133 moles) of sodium carbonate and 24.4 kg (291 moles) of sodium bicarbonate were mixed at 60° C. in another reactor (500 l capacity). The filtrate was heated to 60° C., and was gradually added in droplets to the mixture. Then the mixture was allowed to stand at 80° C. for about three hours. The precipitated calcium carbonate was filtered, which was used in the example 2. The filtrate contained a mixture of tetrasodium tartrate monosuccinate (hereinafter referred to as TMS) and hexasodium tartrate disuccinate (hereinafter referred to as TDS), wherein the mixture had a purity of 88.4 wt % (for all sodium salts of organic acids). The sodium salts of organic acids contained in the filtrate are shown in the Table 1.

EXAMPLE 2

43.6 kg (305 moles, containing 4.2 kg of sodium salts of organic acids) of the calcium carbonate obtained in the example (1) and 78.4 kg of water were mixed at 80° C. in a reactor (500 l capacity), to which 46.6 kg (475 moles) of maleic anhydride was gradually added in droplets over about a period of two hours. Then the mixture was allowed to stand at 80° C. for three hours, to which 51.9 kg (120 moles, containing 8.8 kg of sodium salts of organic acids) of the cake (calcium tartrate) obtained in the example (1), 23.3 kg of water, 263.3 kg (380 moles) of a 28 wt % aqueous solution of disodium DL-tartrate and 4.6 kg (25 moles) of 40 wt % calcium hydroxide slurry were added. In addition, an aqueous solution of 48 wt % sodium hydroxide was added to the mixture to raise the equivalent ratio to 1.01. The pH value was 9.8. The high-performance liquid chromatographic analysis showed that the concentration of organic acid salts was 35.8 wt %.

The slurry obtained was concentrated to 300 kg under a reduced pressure at 70° C. over a period of three hours, to which 22.8 kg (273 moles) of 48 wt % sodium hydroxide was added to raise the equivalent ratio to 1.14. Then the mixture was heated at 75° C. for eight hours. The same procedure followed as the example (1), and the results are shown in the Table (1).

EXAMPLE 3

380 g of water, 150 g (1.0 mol) of DL-tartaric acid and 93 g (0.95 moles) of maleic anhydride were mixed in a flask (1 l capacity), to which 167 g (0.9 moles) of 40 wt % calcium hydroxide slurry and 165 g (1.983 moles) of a 48 wt % aqueous solution of sodium hydroxide were added to prepare a slurry-like mixture having a equivalent ratio of 0.97 and an organic acid salt concentration of about 36 wt %. The mixture was concentrated to 558 g at 70° C. over a period of three hours, and 55 g (0.663 moles) of 48 wt % sodium hydroxide was added to raise the equivalent ratio to 1.14. Then the mixture was heated at 75° C. for eight hours. The concentration of organic acid salt was 60.5 wt %. The same procedure followed as the example (1), and the results are shown in the Table (1).

Comparative Examples 1 to 3

The same process was conducted as the Example 3, except that before concentrating the equivalent ratio was differently adjusted, and that the reaction came to an end when a state of equilibrium was attained with the total amount of TMS and TDS reaching the maximum. The results are shown in the Table (1).

EXAMPLE 4

The same process was conducted as the Example 3, except that the quantity of 48 wt % sodium hydroxide was increased to raise the equivalent ratio to 1.03, and that after concentrating the quantity of 48 wt % sodium hydroxide was also increased to raise the equivalent ratio to 1.20. The results are shown in the Table (1).

TABLE (1)

| Example | Conditions Base/Acid equivalent | | Reactive Products Composition (wt %/organic acid salt) | | | | | Purity (wt %) |
| --- | --- | --- | --- | --- | --- | --- | --- | --- |
| | $T_1$ | $T_2$ | TMS | TDS | TA | MA | FA | |
| (1) | 1.00 | 1.44 | 72.6 | 15.8 | 3.5 | 2.6 | 4.6 | 88.4 |
| (2) | 1.01 | 1.14 | 72.1 | 16.0 | 3.5 | 2.6 | 4.7 | 88.1 |
| (3) | 0.96 | 1.14 | 72.9 | 14.9 | 3.7 | 2.5 | 5.0 | 87.8 |
| Compar. | | | | | | | | |
| (1) | 1.14 | 1.14 | 69.6 | 13.6 | 3.6 | 2.5 | 9.3 | 83.2 |
| (2) | 0.90 | 1.14 | 69.2 | 15.4 | 3.3 | 2.7 | 8.2 | 84.6 |
| (3) | 1.06 | 1.14 | 70.6 | 14.2 | 3.4 | 2.5 | 8.1 | 84.8 |
| Example | | | | | | | | |
| (4) | 1.03 | 1.20 | 78.1 | 9.3 | 3.5 | 2.4 | 5.5 | 87.4 |

(Note)
Compar.: Comparative example
$T_1$: while concentrating
$T_2$: while reacting
TMS: tetrasodium tartrate monosuccinate
TDS: hexasodium tartrate disuccinate
TA: disodium tartrate
MA: disodium maleate
FA: disodium fumarate
Purity: weight percent of total amount of TMS and TDS for all organic acid salts

EXAMPLE 5

1,100 g of water, 134 g (1.0 mol) of malic acid and 118 g (1.2 moles) of maleic anhydride were mixed in a flask (2 l capacity), to which 185 g (1.0 mole) of 40 wt % calcium hydroxide slurry and 203 g (2.44 moles) of 48 wt % sodium hydroxide were added to prepare a slurry-like mixture having an equivalent ratio of 1.01 and an organic acid salt concentration of about 21 wt %. The mixture was concentrated to about 700 g at 70° C. over a period of four hours (having an organic acid salt concentration of about 53 wt %), and 33 g (0.40 moles) of 48 wt % sodium hydroxide was added to raise the equivalent ratio to 1.10. Then the mixture was heated at 75° C. for five hours. The concentration of organic acid salt was 55 wt %. As in the example (1), sodium carbonate and sodium bicarbonate were added to allow the calcium content to precipitate in the form of calcium carbonate. In this way a filtrate containing tetrasodium oxydisuccinate was obtained, which had a purity of 71 wt % (for all sodium salts of organic acids).

Comparative Example 4

Unlike the example (5), 236 g (2.84 moles) of 48 wt % sodium hydroxide was added at one time at the initial stage, where the base equivalent/the acid equivalent was 1.10. After the reaction was conducted, the concentration of organic acid salt was about 55 wt %. The mixture was concentrated over a period of eight hours. The other processes were the same as in the example (5). The tetrasodium oxydisuccinnate had a purity of 65 wt % (for all sodium salts of organic acid).

What is claimed is:

1. A process for producing an alkali metal and zinc and/or alkaline earth metal salt of an ethercarboxylic acid, which comprises concentrating an aqueous mixture containing (a) maleic acid and/or maleic anhydride, (b) oxycarboxylic acid, (c) alkali metal, and (d) zinc and/or alkaline earth metal, wherein the equivalent ratio of the total base equivalent of (c) alkali metal and (d) zinc and/or alkaline earth metal to the total acid equivalent of (a) maleic acid and/or maleic anhydride and (b) oxycarboxylic acid falls in the range of 0.93 to 1.04, and adding alkali metal to adjust the equivalent ratio to the range of 1.05 to 2.0 so as to effect an addition reaction between the maleic acid and the oxycarboxylic acid.

2. A process as set forth in claim 1, wherein the aqueous mixture contains (a) maleic acid and/or maleic anhydride, (b) oxycarboxylic acid, and (d) zinc and/or alkaline earth metal at the mol ratio of 0.2–10:1:0.1–5.0, respectively, wherein the total moles of (d) zinc and/or alkaline earth metal is not greater than that of (a) maleic acid and/or maleic anhydride and (b) oxycarboxylic acid.

3. A process as set forth in claim 1, further comprising adding organic acid or inorganic acid or water to the aqueous mixture after the addition reaction is finished, thereby allowing any unreacted oxycarboxylic acid to precipitate and segregate in the form of a metallic salt.

4. A process as set forth in claim 1, further comprising contacting an alkali metal carbonate and/or bicarbonate with the product containing said salt of ethercarboxylic acid, thereby segregating the zinc carbonate and/or alkaline earth metallic carbonate.

5. A process as set forth in claim 4, further comprising contacting the segregated zinc carbonate and/or alkaline earth metallic carbonate with maleic acid and/or maleic anhydride in an aqueous medium so that zinc maleate and/or alkaline earth metallic maleate are produced and recycled for use in producing the said salt of ethercarboxylic acid.

6. A process as set forth in claim 1, wherein the oxycarboxylic acid is tartaric acid.

7. A process as set forth in claim 6, wherein the aqueous mixture is concentrated until the alkali metallic salt has a concentration of at least 45 wt % when it is calculated on the presumption that all the carboxyl group in the maleic acid and the oxycarboxylic acid is replaced by alkali metallic salt.

8. A process as set forth in claim 6, wherein the ethercarboxylic acid is tartaric monosuccinic acid and/or tartaric disuccinic acid.

9. A process as set forth in claim 1, wherein the metal salt of ethercarboxylic acid is alkali metal salt of ethercarboxylic acid.

10. The process of claim 1, wherein (d) is zinc.

11. The process of claim 1, wherein (d) is a combination of zinc and calcium.

12. The process of claim 1, wherein (d) is a combination of zinc, calcium and magnesium.

13. The process of claim 1, wherein (d) is a combination of calcium and magnesium.

14. The process of claim 1, wherein (d) is calcium.

* * * * *